United States Patent
Moreyra (10) Patent No.: US 6,969,385 B2
(45) Date of Patent: Nov. 29, 2005

(54) WRIST WITH DECOUPLED MOTION TRANSMISSION

(76) Inventor: Manuel Ricardo Moreyra, 2718 NE. 195th Pl., Seattle, WA (US) 98155

( * ) Notice: Subject to any disclaimer, the term of this patent is extended or adjusted under 35 U.S.C. 154(b) by 133 days.

(21) Appl. No.: 10/384,298

(22) Filed: Mar. 6, 2003

(65) Prior Publication Data
US 2003/0208186 A1  Nov. 6, 2003

Related U.S. Application Data

(60) Provisional application No. 60/376,964, filed on May 1, 2002.

(51) Int. Cl.[7] ............................................. A61B 17/00
(52) U.S. Cl. ........................... 606/1; 74/490.01; 901/29
(58) Field of Search ...................... 606/1, 208; 901/27, 901/28, 29, 30; 74/490.01, 490.02, 490.06

(56) References Cited

U.S. PATENT DOCUMENTS 6,394,998 B1 * 5/2002 Wallace et al. ................. 606/1

* cited by examiner

Primary Examiner—Rosiland Rollins (57) ABSTRACT

The present invention is a wrist mechanism and a method for making robotic devices in which the transmission of motion, force and/or torque around a revolute joint can be accomplished without coupling. This construction allows mounting the actuators on the base or lower elements of a mechanism, so that only linkage elements move the end-effector. Thus reducing inertia of the moving elements and increasing performance of the device. The decoupled motion of the end-effector or links is achieved by routing their transmission cables around idler pulleys placed parallel to the joint rotation axis on an optimal position such any stretch on the transmission cable is minimized. In particular, this construction can be use for robotic surgical tools that have two independently driven jaws, decoupled and orthogonal from its articulating wrist. This device may be used in grasping, cutting, suturing or alike operations.

18 Claims, 7 Drawing Sheets

WRIST WITH DECOUPLED MOTION TRANSMISSION

CROSS-REFERENCE TO RELATED APPLICATIONS

This application claims priority from commonly owned U.S. Provisional Patent Application No. 60/376,964, filed May 1, 2002 titled Articulated Wrist And Tool With Decoupled Motion Transmission, presently pending, which is hereby incorporated by reference in its entirety.

BACKGROUND OF THE INVENTION

Minimally invasive surgical robotic systems are being developed to increase surgeon's dexterity when working within an internal surgical location. Such minimally invasive procedures are conducted by inserting surgical instruments through small incisions on the skin of the patient. The use of dexterous surgical instruments to manipulate tissues and suture would facilitate the performance of an endoscopic surgical procedure. A manually or robotically actuated surgical device that can articulate as well as actuate reliably would minimize patient risk and operating time.

Current minimally invasive surgical tools have many drawbacks. Most endoscopic tools have rigid shafts and are constrained to approach the workspace from the direction of a small incision. In addition, many robotic devices often have their motors or actuators mounted on the adjacent links. When these motors are mounted on moving links, their weight often reduces the performance of the device. Sometimes the volume that motors occupy near the end-effector can interfere with the access to a workspace. Furthermore, the construction and length of many endoscopic instruments reduces the surgeon's ability to feel the force exerted by tissues and organs on the end-effector. The limited dexterity and sensitivity provided by endoscopic tools is a major obstacle to the improvement and expansion of minimally invasive surgery.

Surgical tools that increase the surgeons' dexterity are needed to improve minimally invasive surgery procedures. It is desirable to provide surgical instruments having a wrist with two or tree degrees-of-freedom. It is further desirable to provide a wrist mechanism that has low friction in order to provide the surgeon with sensitivity feedback of the contact forces exerted by the surgical tools. Furthermore, it is desirable to minimize the stretch in a cable operatively coupling a portion of the tool that is inserted through the incision with power and control mechanisms that remain outside the incision.

SUMMARY OF INVENTION

The present invention provides a wrist in which the transmission of motion, force and/or torque around a revolute joint can be accomplished without coupling. The motion of its adjacent link does not affect the relative motion of the decoupled element. This construction allows mounting the actuators on other elements of a mechanism, so that only linkage elements move the end-effector. Thus reducing inertia of the moving elements and increasing performance of the device. The decoupled motion of the end-effector or links is achieved by routing their transmission cables around idler pulleys placed parallel to the joint rotation axis on an optimal position such that any stretch on the transmission cable is minimized. This construction may be use for robotic surgical tools that have two independently driven jaws, decoupled and orthogonal from its articulating wrist. This surgical device may also be used in grasping, cutting, suturing or alike operations.

The wrist includes a base that may be mounted to an arm or other structure that locates the wrist away from a drive mechanism. The wrist also includes a link having an end-effector portion that may be pivotally attached to an end-effector to allow the end-effector to pivot about a link axis, and a base portion that is pivotally attached to the base and operable to pivot about a wrist axis of the base. The wrist also includes an idler having a diameter and rotatably attached to the base such that the idler is operable to rotate about an idler axis that is offset from the wrist axis. A cable operatively couples the end-effector to a drive mechanism to allow a user to operate the end-effector. The offset of the idler axis is calculated to minimize stretch in the cable as the link pivots about the wrist axis. Thus, the cable is less likely to develop a permanent stretch over multiple uses, which can cause backlash and adversely affect the sensitivity or "feel" a user often requires while operating the end-effector. Furthermore, when a user pivots the end-effector relative to the link and pivots the end-effector relative to the wrist, one of the motions does not affect the other motion, i.e., the motions are independent of each other.

The offset that provides the minimal stretch in the cable over a desired range of motion, such as pivoting the link 180°, or 120° depends on the desired range of motion, the idler diameter and the ratio of the idler diameter to the distance between the link axis and the wrist axis. For example, the offset that provides the minimal stretch in the cable over a 180° range of motion with an idler pulley diameter of 5 millimeters (mm) and a 12.5 mm distance between the link axis and the wrist axis is 1.48 mm. For the same range of motion but other idler diameters and other distances between the link axis and the wrist axis the offset can be calculated from the following ratios $D_w/D_i$ $C_s/D_i$
Infinite 0.2854
100 0.2859
50 0.2863
10 0.2903
5 0.2959
3 0.3049

Where $D_w$ is twice the distance between the link axis and the wrist axis (diameter); $D_i$ is the diameter of the idler and $C_s$ is the offset distance. So for a given ratio of the distance between the link and wrist axes to the diameter of the idler pulley, the offset can be calculated by multiplying the diameter of the idler by the number provided in the chart.

In one embodiment of the wrist, the idler axis is parallel or substantially parallel to the wrist axis and the link axis is perpendicular or substantially perpendicular to the wrist axis. In addition, the wrist may include at least two idlers. For example, the wrist may include eight idlers in four groups of two, with the two idlers in each group concentric with each other and each idler is operable to pivot about one of four respective idler axes that are each offset from the wrist axis.

DESCRIPTION OF PREFERRED EMBODIMENTS

FIGS. 1 through 4 illustrate a wrist and tool 10. The end-effector consists of two jaws 40.1 and 40.2, each jaw is rigidly coupled to their respective drive pulleys 42.1 and 42.2. Both jaws rotate around a link axis α on a common shoulder screw 41 that is mounted to the link 30. An orthogonal wrist rotation β occurs when the jaws base rotates with its pulley 33 around pin 31.

Figure 4:
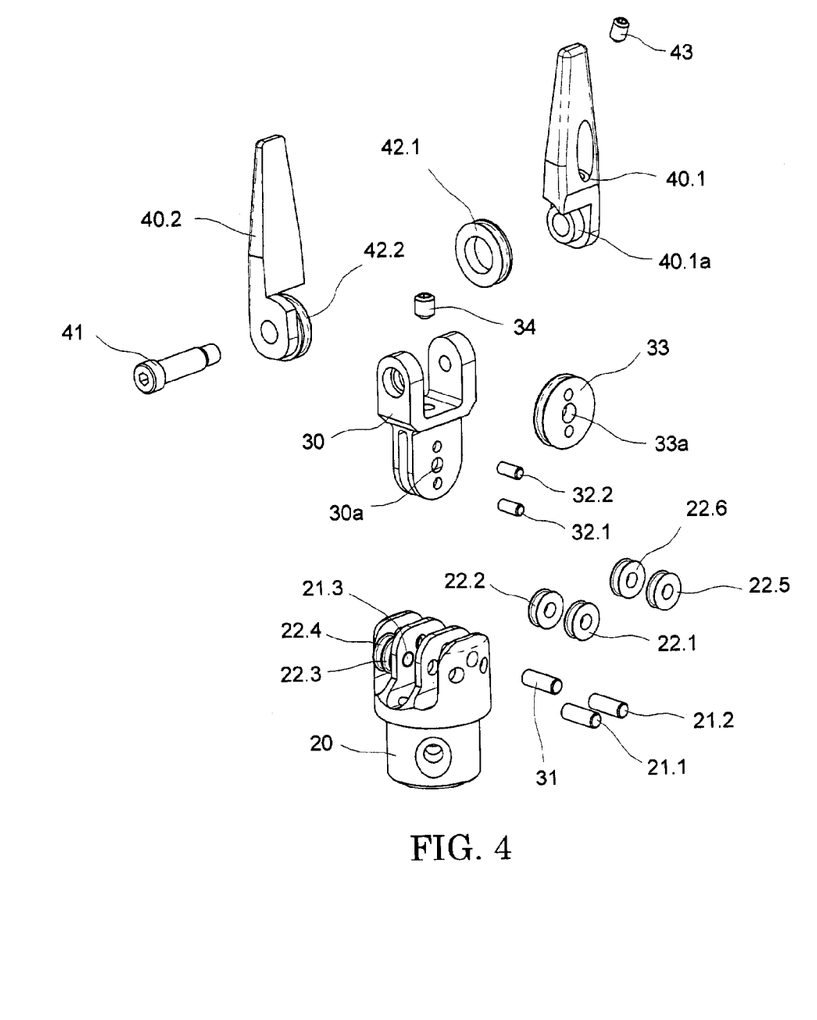
FIG. 4 is an exploded perspective view of the wrist mechanism of FIGS. 1–3 according to an embodiment of the invention.

FIG. 4 shows an exploded view of the wrist mechanism 10. The jaw 40.1 has a ring 40.1a machined around its rotation axis. Each drive pulley 42.1 and 42.2 mounts on its jaw ring with its respective cable attached. Each jaw 40.1 and 40.2, pulley 42.1 and 42.2, and the cable 50.1 and 50.2 (not shown in FIG. 4) is rigidly coupled together with its setscrew 43.

Each jaw 40.1 and 40.2 can rotate independently around the shoulder screw 41, α axis. When the two jaws rotate on the same direction, one wrist articulation motion is accomplished. And when the jaws rotate on opposite direction, the jaws will open or closed. The jaws motions are driven through their cables 50.1 and 50.2. These cable are routed through guiding idler pulleys 22 from their distal drive mechanism.

The link 30 mounts to its pulley 33 with two pins 32. The setscrew 34 couples rigidly the jaw base 30 and pulley 33 with its cable 50.3 (not shown in FIG. 4). The jaw base subassembly is then mounted on the center slot of the wrist base 20 with pin 31. This subassembly pivots on the jaw base center hole 30a, about the wrist axis β. The pulley center hole 33a is larger than the base center hole 30a to avoid binding when the setscrew 34 presses down the cable and pulley.

There are four pairs of idler pulleys 22, two pairs per jaw; they mount between the two lateral slots of the wrist base 20 with pins 21. These idlers guide the jaw cables 50.1 and 50.2 from the jaw pulleys 42.1 and 42.2 to the drive mechanism. Note that there are four pins 21 for the idlers, two pins per side. Pins 21 cannot go through the whole wrist base 20 because they would interfere with the link 30 and it pulley 33.

Figures 5, 6, 7:
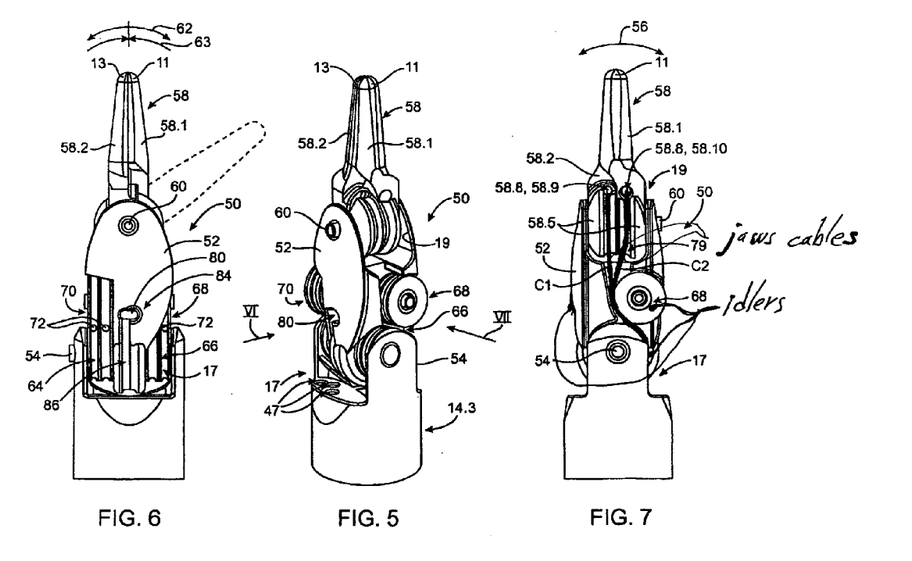
FIG. 5 is a schematic top view of a wrist mechanism with an end-effector pivoted 90° about a wrist axis and illustrates a path of a cable used to pivot the end-effector, according to an embodiment of the invention.
FIG. 6 is a schematic front view of a wrist mechanism without idler pulleys and illustrates the lack of cable stretch as the end-effector pivots about a wrist axis.
FIG. 7 is a schematic front view of a wrist mechanism with idler pulleys located to minimize cable stretch as the end-effector pivots about a wrist axis, according to an embodiment of the invention.
Figure 5:
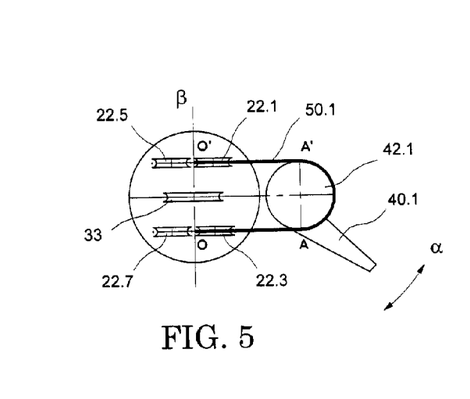
Figure 6:
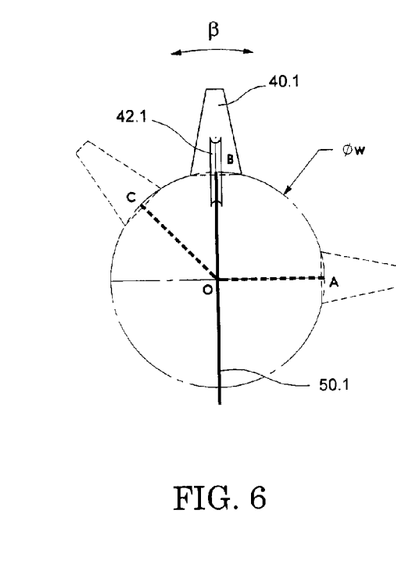
Figure 7:
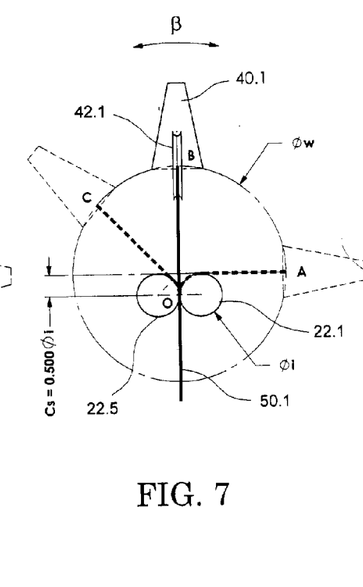

FIGS. 5 through 8 illustrate schematic wrist drawings to determine an optimal geometry such that the length of the transmission cable 50.1 remains approximately constant for β between −90° and 90°. FIG. 5 shows a schematic top view of the wrist, the pulley cable 50.1 is shown with thick line with wrist articulation β rotated 90° with respect to its tube axis. The cable detaches from the jaw pulley 42.1 at A and A'. Also the cable detached from the idler pulleys 22.1 and 22.5 at O and O'.

FIG. 6 is a schematic front view of the wrist, it shows the cable routing at three different angles β: AO when β is 90°; BO when β is 0°; and CO when β is −45°. If cable 50.1 turns on a sharp corner, no idlers 22, then the cable length would be constant at any angle β:

$$AO = BO = CO$$

But sharp or small round edges would wear the transmission element (cable, belt, etc.) fast and increase friction. Also transmission elements required a minimum turning radius to increase their useful life. Therefore idler pulleys are required to guide the cable.

FIG. 7 is a schematic front view of the wrist as FIG. 6, but there are idler pulleys 22.1 and 22.5 located such that their center is 0.50 $\varnothing_i$ below the center of β axis. For this case:

$$AO = 0.5(\varnothing_w + \varnothing_i(\pi-1))$$

$$BO = 0.5(\varnothing_w + \varnothing_i)$$

The difference is:

$$BO - AO = \varnothing_i(1 - \pi/4) = 0.2146\,\varnothing_i$$

Figure 8:
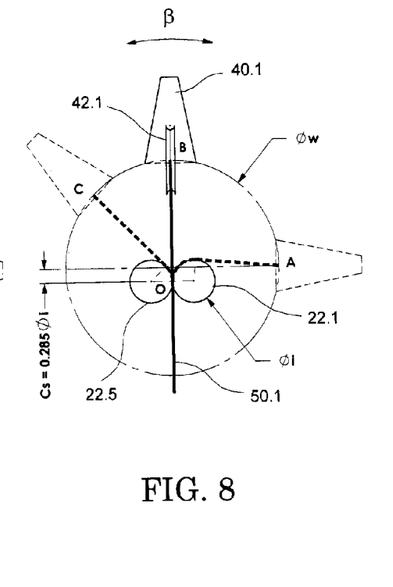
FIG. 8 is a schematic front view of a wrist mechanism with idler pulleys located in another position to minimize cable stretch as the end-effector pivots about a wrist axis, according to an embodiment of the invention.

FIG. 8 is a schematic front view of the wrist as FIG. 7, but the idler pulleys 22 have been shifted upward 0.215$\varnothing_i$, such that their centers are 0.285$\varnothing_i$ below the center of β axis. When $\varnothing_i \ll \varnothing_w$ and $C_s = 0.285\varnothing_i$, we get:

$$AO \approx BO \approx CO$$

The cable length remains approximately constant for any angle of β between −90° and +90°. The optimal offset $C_s$ is sensitive to the $\varnothing_i/\varnothing_w$ ratio. The optimal $C_s$ to minimize cable stretch for a very large $\varnothing_i/\varnothing_w$ ratio is 0.2854$\varnothing_i$. For a $\varnothing_i/\varnothing_w = 100$ ratio, the optimal offset $C_s = 0.2859\varnothing_i$; for $\varnothing_i/\varnothing_w = 50$ the optimal $C_s = 0.2863\varnothing_i$; for $\varnothing_i/\varnothing_w = 10$ the optional $C_s = 0.2903\varnothing_i$; for $\varnothing_i/\varnothing_w = 5$ the optimal $C_s = 0.2959\varnothing_i$; and for $\varnothing_i/\varnothing_w = 3$ optimal $C_s = 0.3049\varnothing_i$.

Figure 1:
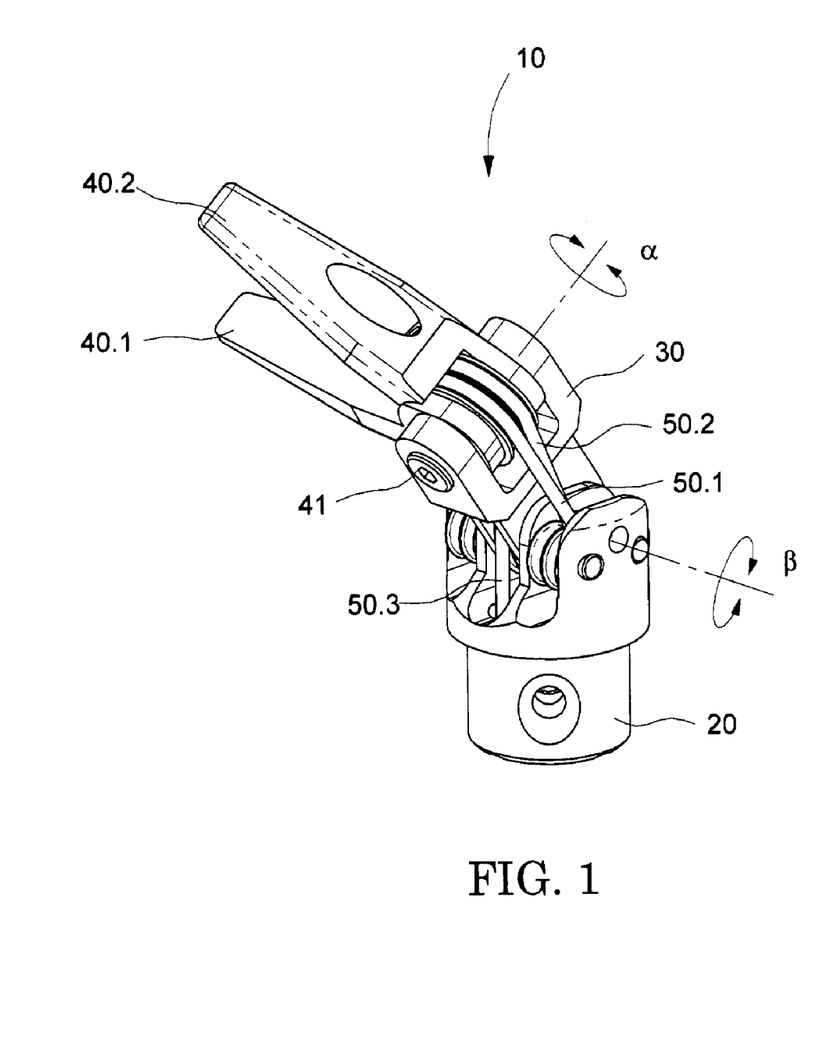
FIG. 1 is a perspective view of a wrist mechanism according to an embodiment of the invention.

In particular, the embodiment shown in FIG. 1 has the following dimensions (mm): $\varnothing_w = 25.0$; $\varnothing_i = 5.0$; $C_s = 1.48$; and the diameter of the jaw pulley is 8 mm. Consequently, $\varnothing_w/\varnothing_i = 5.0$ and $C_s = 0.296\varnothing_i$. The maximum cable length, AO=13.98, occurs when β=0°, −90° and 90°. The minimum cable length is 13.69 when β=61°. So the cable stretches 0.29 mm (2.1%) between its minimum and maximum lengths.

Figure 9:
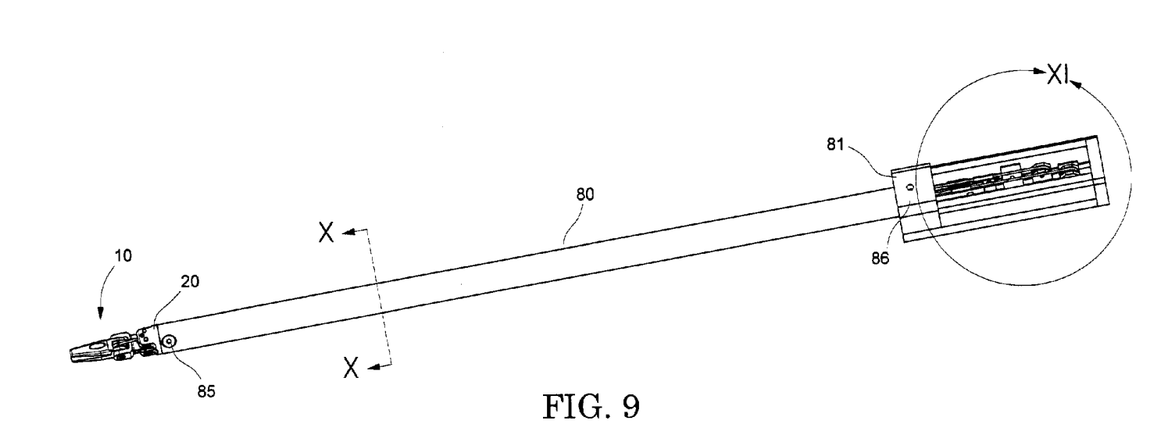
FIG. 9 is a perspective view of a tool incorporating the wrist mechanism of FIGS. 1–3 according to an embodiment of the invention.
Figure 10:
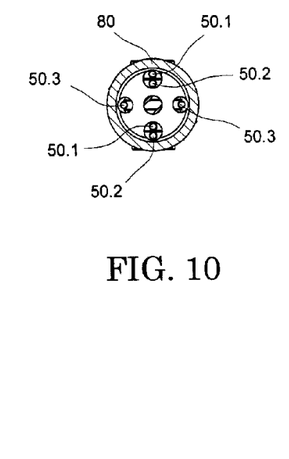
FIG. 10 is a cross-sectional view of the tool in FIG. 9 showing cables disposed within a tube, according to an embodiment of the invention.

But if the wrist is mounted in embodiments as the ones shown in FIGS. 9 and 10, the drive system is locate distal from the wrist and they are connected through an elongated arm. The total lengths of the cable loops on the embodiment shown on FIGS. 9 and 10 are about 800 mm each. So the 0.29 mm stretch that occurs equally on each side of the jaws pulleys represent only 0.073% of the total cable length, less than one thousand stretch. For most mechanical systems a variation of less than one thousand of the length of their transmission element is negligible. Also, the stretch is equal on each end of the jaws pulleys 42, consequently the motion of the jaws 40 are decoupled from the wrist motion.

In general, this invention presents a method for guiding transmission cables around joints while minimizing the stretch in cable. Any mechanism with its particular $\varnothing_i/\varnothing_w$ ratio, and range of motion β, can be designed using this method for minimizing cable stretch. For example: if the wrist shown in FIG. 1 would have a reduced range of motion, rotate an angle β between −60° and +60°, then cable stretch can be minimized by adjusting $C_s$ as follows; start with the optimal $C_s$=1.48 mm (optimal for ±90° range of motion); shift the idler pulleys 22 upwards a distance equal to the maximum stretch for this range or motion, or 0.29 mm; the new $C_s$=1.19 mm, and the new maximum stretch has been reduce to 0.164 mm; repeat shifting position upward until a minimum is found; the new optimal idlers 22 position is at Cs=0.926 mm and the stretch has been reduced to 0.078 mm, only about one quarter the stretch the occurs for a ±90° range of motion.

FIG. 9 shows the wrist 10 connected to a driver mechanism, located away from the wrist mechanism, through the tube 80. The tube 80 mounts to the wrist base with screw 85, and to the idlers base 81 with setscrew 86. By locating the driver mechanism away from the wrist mechanism, the cable stretch that occurs at different β angles is spread over the whole length of the cable. Consequently, any small change of cable length that occurs on the wrist is negligible over the whole cable length.

FIG. 10 illustrates a section view of the bottom of the wrist; it shows the arrangement of the transmission cables 50. The cables run through the inside of the tube, which shields the cable.

Figure 11:
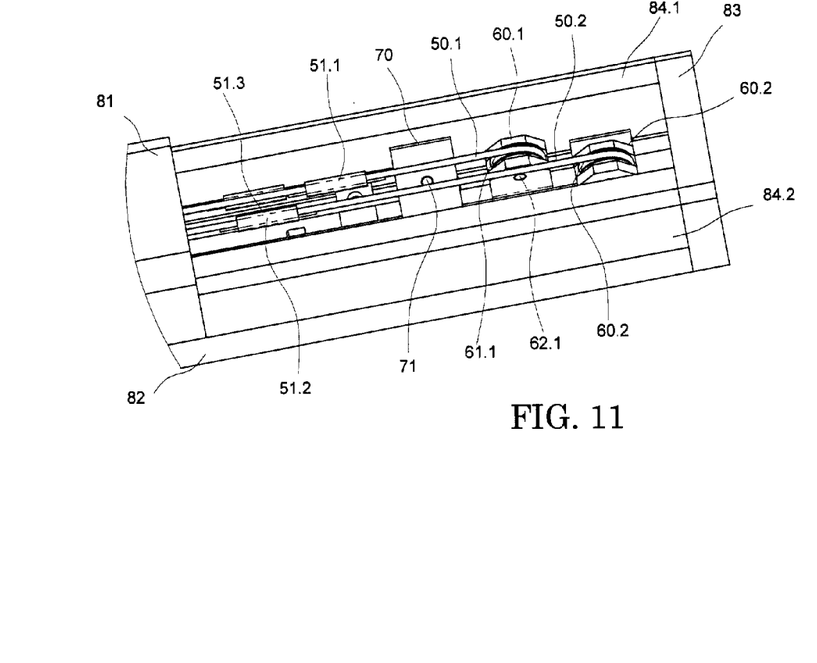
FIG. 11 is a detail view of the driver mechanism in FIG. 9.

FIG. 11 illustrates a detail view of the driver mechanism. This driver mechanism comprises of pulley hangers 60.1, 60.2 and 70 that slide on a dovetail groove located on the idlers guide 82. Pulling the hangers with screws mounted on the rear plate 83 sets the cable tension. Crimped loop sleeves 51 are used for joining the two ends of an open cable. To rotate the wrist or jaws around their axes, one pulls their respective cable relative to the tube. In other embodiment the cables can be pulled by actuators or motors powered by electricity, compressed air or hydraulic fluid.

Figure 12:
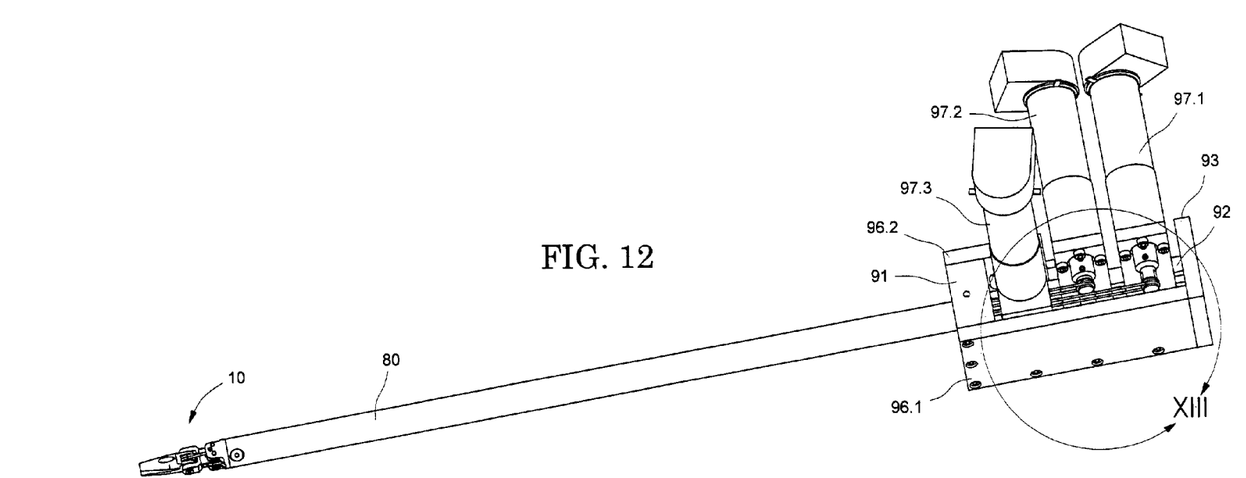
FIG. 12 is a perspective view of a tool incorporating the wrist mechanism of FIGS. 1–3 according to another embodiment of the invention.
Figure 13:
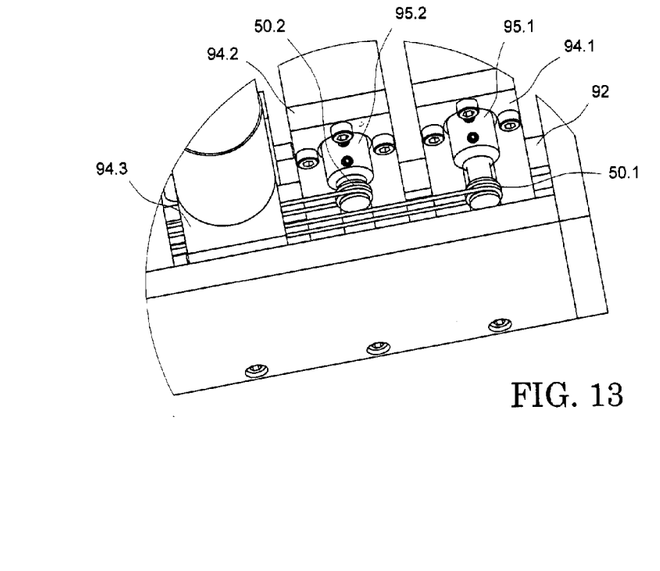
FIG. 13 is a detail view of the driver mechanism in FIG. 12.

FIG. 12 shows the wrist 10 connected to another distal driver mechanism through the tube 80. The tube 80 mounts to the driver's base 91 with setscrew 86. FIG. 13 illustrates a detail view of the drive mechanism; it shows how the jaw cables 50.1 and 50.2 mount around their driver pulleys 95.1 and 95.2. These cables loop a few times around their pulleys 95 (capstan) such that friction allows the motors 97 to properly drive the cables within a limited range of motion, typically wrist and jaws motions between −90° and 90°. The motor mounts 94 slides on dovetail grooves located on the driver guide 92. Pulling the motor mounts with screws mounted on the rear plate 93 sets the cable tension.

Figures 14, 15:
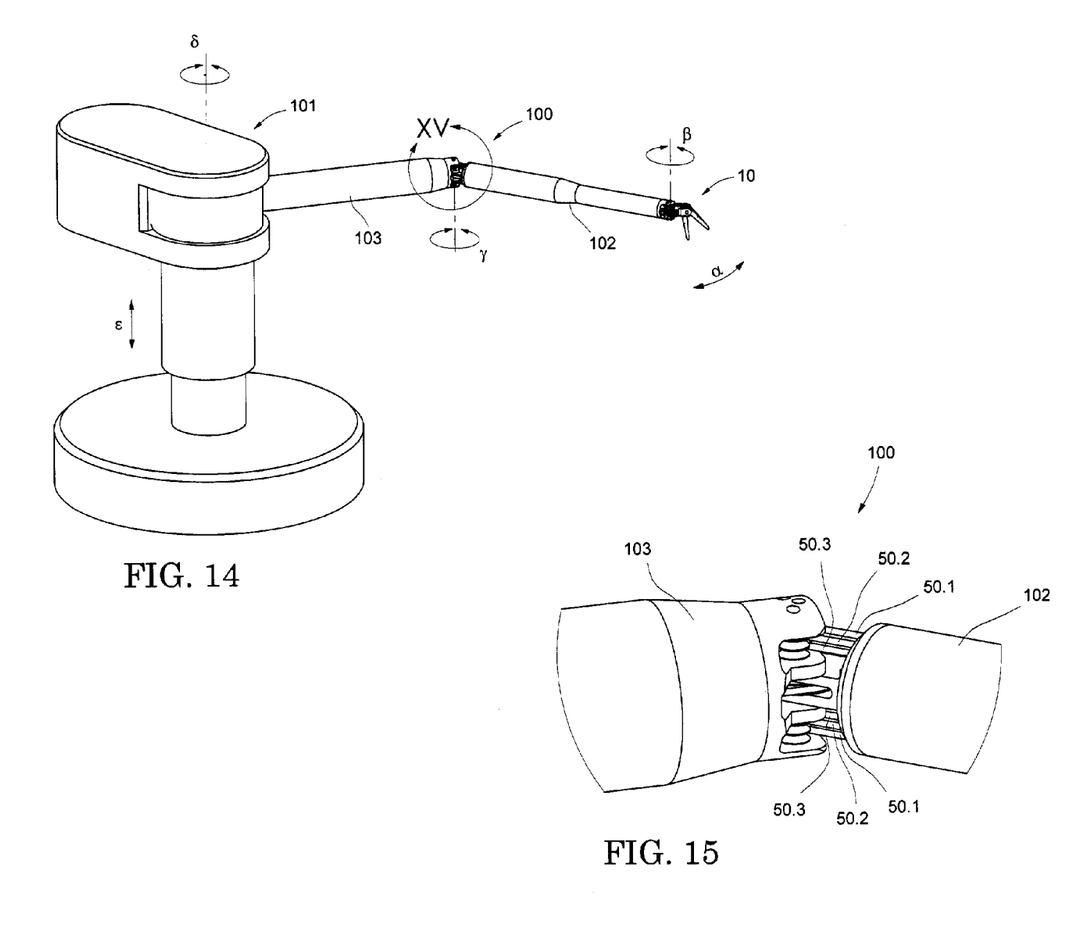
FIG. 14 is an illustration of an alternative grasper configuration with the jaws and wrist transmission cable routed through an intermediate joint.
FIG. 15 is a detail view of a joint of the mechanism in FIG. 14.

FIG. 14 shows an alternative five axes embodiment in which the motors, for driving the wrist 10 links and the arm 102, are located on a motor housing 101. The wrist transmission cables are routed through the hollow arms 102 and 103, are around the joint 100 idler pulleys. FIG. 15 illustrates a detail view of the joint 100. The wrist cables 50.1, 50.2 and 50.3 are guided around joint 100 by their respective idlers, which are location at an optimal position to minimize cable stretch.

What is claimed is:

1. A wrist for minimizing stretch in a cable coupling an end-effector and a drive mechanism, the wrist comprising:
   a base having a wrist axis;
   a link operable to pivot about the wrist axis and including an end-effector portion attachable to an end-effector, and a base portion pivotally attached to the base, the end-effector portion having a link axis about which the end-effector can rotate; and
   an idler that is attached to the base and that rotates about an idler axis that is offset from the wrist axis.

2. The wrist of claim 1 wherein the idler is a pulley.

3. The wrist of claim 1 wherein the idler axis is parallel or substantially parallel to the wrist axis.

4. The wrist of claim 1 wherein the link axis is perpendicular or substantially perpendicular to the wrist axis and does not intersect the wrist axis.

5. The wrist of claim 1 wherein the wrist includes at least two idlers operable to rotate about the idler axis.

6. The wrist of claim 1 wherein the wrist includes eight idlers attached to the base in four groups of two, each idler is a pulley having a diameter, and the two idlers in each group are concentric with the each other, and wherein each idler is operable to pivot about one of four respective idler axes that are each offset from the wrist axis, and each group is disposed between the base and the link.

7. The wrist of claim 1 wherein:
   the link includes a link diameter that is 5 millimeters,
   the link axis is located 12.5 millimeters from the wrist axis, and
   the idler axis is offset 1.5 millimeters from the wrist axis.

8. The wrist of claim 1 wherein the link rotates 180° about the wrist axis.

9. The wrist of claim 8 wherein:
   the end-effector includes a first and second jaw opposing each other;
   a first cable is coupled to the first jaw and operable to pivot the first jaw about the link axis; and
   a second cable is coupled to the second jaw and operable to pivot the second jaw about the link axis.

10. The wrist of claim 9 wherein the jaws can be pivoted about the link axis independent of each other.

11. The wrist of claim 1 further comprising an end-effector pivotally attached to the end-effector portion of the link and operable to pivot about the link axis and wherein the motion of the link about the wrist axis is independent from the motion of the end-effector about the link axis.

12. The wrist of claim 11 further comprising a cable coupled to the end-effector and operable to pivot the end-effector about the link axis, wherein when the link is pivoted about the wrist axis and the end-effector is pivoted about the link axis, a portion of the cable contacts the idler.

13. A tool for grasping, cutting, clamping, moving items, comprising:
   an arm;
   a wrist including:
      a base having a wrist axis,
      a link operable to pivot about the wrist axis and including an end-effector portion attachable to an end-effector, and a base portion pivotally attached to the base, the end-effector portion having a link axis about which the end-effector can rotate; and an idler that is attached to the base and that rotates about an idler axis that is offset from the wrist axis, and an end-effector pivotally attached to the end-effector portion and operable to pivot about the link axis;

a cable coupled to the end-effector and operable to pivot the end-effector about the link axis, wherein when the link is pivoted about the wrist axis and the end-effector is pivoted about the link axis, a portion of the cable contacts the idler;

a drive mechanism coupled to the cable and operable to pivot the end-effector about the link axis.

14. The tool of claim 13 wherein the drive mechanism includes an actuator operable to pivot the end-effector about the link axis.

15. The tool of claim 13 wherein the drive mechanism includes a pulley hanger operable to pivot the end-effector about the link axis.

16. The tool of claim 13 further comprising a wrist cable coupled to the link of the wrist and operable to pivot the link about the wrist axis.

17. The tool of claim 13 wherein the arm includes two sections and a second wrist pivotally attaching the two sections together wherein the second wrist includes:

a second base having a wrist axis, a second link including an end-effector portion having a link axis and a second base portion pivotally attached to the second base and operable to pivot about the wrist axis of the second base, and a second idler having a diameter and rotatably attached to the second base, wherein the second idler is operable to rotate about an idler axis that is offset from the wrist axis of the second wrist.

18. A method for minimizing stretch in a cable that couples an end-effector to a drive mechanism, the method comprising:

pivotally attaching a link of a wrist to a base of the wrist, wherein the link can pivot about a wrist axis;

pivotally attaching an idler to the base such that the idler pivots about an idler axis that is offset from the wrist axis; and contacting the idler with a cable attached to the end-effector when the link is pivoted about the wrist axis.

* * * * *

UNITED STATES PATENT AND TRADEMARK OFFICE
CERTIFICATE OF CORRECTION

Figure 2:
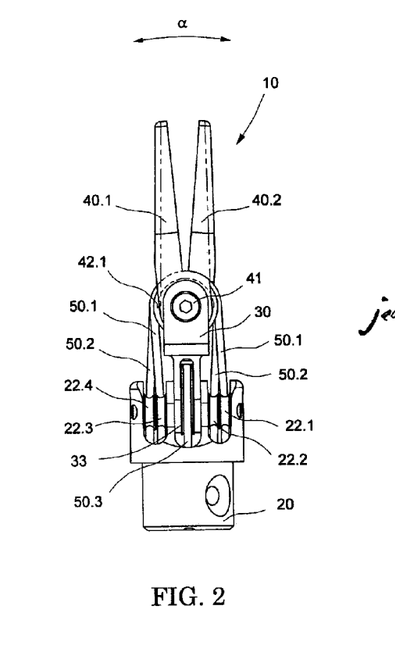
FIG. 2 is a front view of the wrist mechanism shown in FIG. 1 according to an embodiment of the invention.
Figure 3:
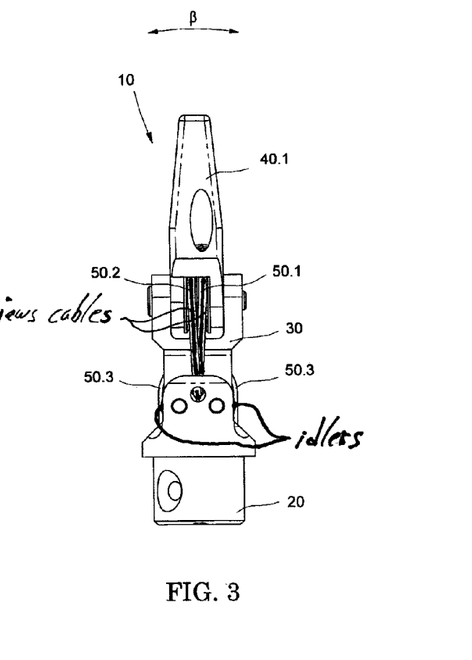
FIG. 3 is a side view of the wrist mechanism shown in FIG. 1 according to an embodiment of the invention.

PATENT NO. : 6,969,385 B2
APPLICATION NO. : 10/384298
DATED : November 29, 2005
INVENTOR(S) : Manuel R. Moreyra It is certified that error appears in the above-identified patent and that said Letters Patent is hereby corrected as shown below:

The drawing sheet 2 of 7 consisting of figures 2 through 7, should be replaced with correct sheet 2 of 7 consisting of figures 2 and 3, included on attached sheet.

Signed and Sealed this

Third Day of April, 2007

JON W. DUDAS
*Director of the United States Patent and Trademark Office*

FIG. 3

FIG. 2